United States Patent [19]

Hochstein et al.

[11] 4,388,154
[45] Jun. 14, 1983

[54] ISOLATION OF ACETALDEHYDE AND METHANOL FROM REACTION MIXTURES RESULTING FROM THE HOMOLOGIZATION OF METHANOL

[75] Inventors: Waldheim Hochstein, Freinsheim; Gerd Kaibel, Lampertheim; Franz-Josef Mueller, Wachenheim; Horst Hartmann, Boehl-Iggelheim, all of Fed. Rep. of Germany

[73] Assignee: BASF Aktiengesellschaft, Fed. Rep. of Germany

[21] Appl. No.: 259,655

[22] Filed: May 1, 1981

[30] Foreign Application Priority Data

May 23, 1980 [DE] Fed. Rep. of Germany ....... 3019765

[51] Int. Cl.³ ............................................ B01D 3/14
[52] U.S. Cl. ....................................... 203/35; 203/61; 203/DIG. 23; 568/913

[58] Field of Search ............... 568/492, 594, 487, 913; 203/28, 34, 35, DIG. 23, 71, 73, 74, 75, 77, 78, 80, 81, 82, 84, 91, 94, 98, 39, 41, 61

[56] References Cited

U.S. PATENT DOCUMENTS

| | | | |
|---|---|---|---|
| 2,757,203 | 7/1956 | Hale | 568/913 |
| 2,839,569 | 6/1958 | Kramer | 568/913 |
| 3,062,889 | 11/1962 | Murphy | 568/492 |
| 4,201,868 | 5/1980 | Slinkard | 560/232 |

FOREIGN PATENT DOCUMENTS 738654 10/1955 United Kingdom.

Primary Examiner—Frank Sever
Attorney, Agent, or Firm—Keil & Witherspoon

[57] ABSTRACT

A process is provided wherein acetaldehyde and methanol are obtained from reaction mixtures which result from the homologization of methanol and which in addition to acetaldehyde essentially contain acetaldehyde dimethylacetal, methanol, methyl acetate and water.

7 Claims, 2 Drawing Figures

Figure 1:
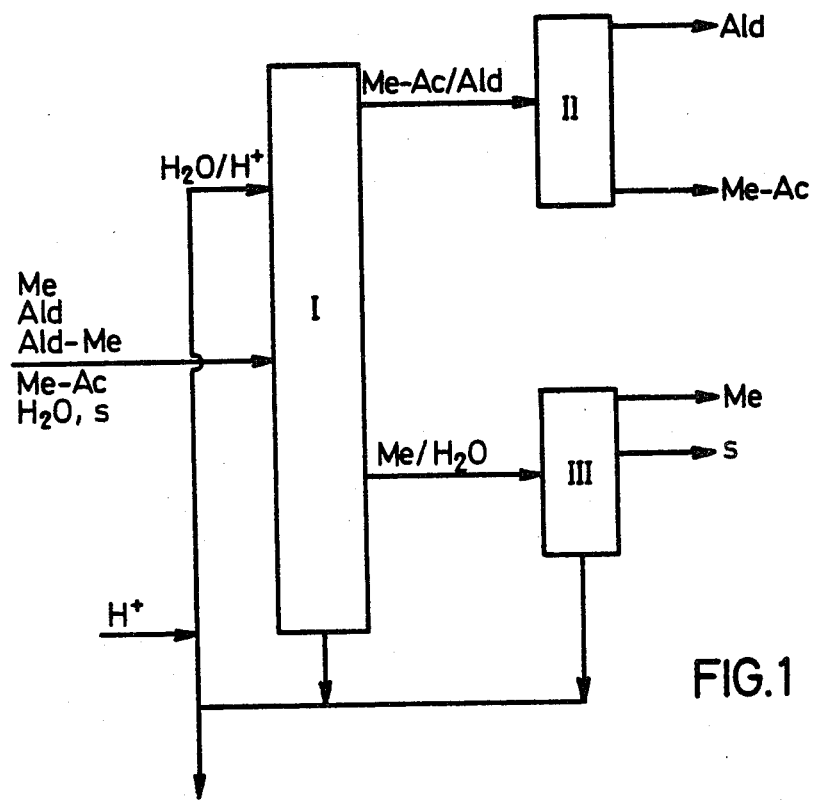

Me = Methanol
Ald = Acetaldehyde
Ald-Me = Acetaldehyddimethylacetal
Me-Ac = Methylacetate
s = remainder
( ) = small quantities Me = Methanol
Ald = Acetaldehyde
Ald-Me = Acetaldehyddimethylacetal
Me-Ac = Methylacetate
s = remainder
( ) = small quantities Legend see FIG.1

ISOLATION OF ACETALDEHYDE AND METHANOL FROM REACTION MIXTURES RESULTING FROM THE HOMOLOGIZATION OF METHANOL

The present invention relates to a process for isolating acetaldehyde and methanol from reaction mixtures resulting from the homologization of methanol.

Homologization means the reaction of an alcohol with carbon monoxide and hydrogen at an elevated temperature and superatmospheric pressure, in the presence of a metal carbonyl complex, for example a cobalt carbonyl complex. Details concerning this reaction may be found in the monograph by Falbe "Chemierohstoffe aus Kohle", Georg-Thieme-Verlag, 1977, page 329 et seq.

In the case of the homologization of methanol, mixtures of numerous compounds are obtained, the relative proportions depending on the reaction conditions. In these mixtures, the most important components, forming in substantial amounts, are the starting material methanol, and the homologization products ethanol, acetaldehyde, acetaldehyde, dimethylacetal, acetic acid, methyl acetate and water. If the reaction is run with relatively low conversion, ethanol formation is substantially suppressed and mixtures essentially containing the following compounds are obtained:

30–75% by weight of methanol
2–10% by weight of acetaldehyde
8–30% by weight of acetaldehyde dimethylacetal
5–10% by weight of methyl acetate and
10–20% by weight of water.

Such mixtures, rich in acetaldehyde, are generally to be preferred, since acetaldehyde has a greater variety of uses than has the ethanol which is the principle product at high conversions. However, working up of such mixtures by distillation presents considerable difficulties, because the acetaldehyde dimethylacetal must be cleaved in order to obtain acetaldehyde, and because both acetaldehyde dimethylacetal and methyl acetate form azeotropes with methanol, so that the methanol cannot be directly recovered.

It is an object of the present invention to separate the acetaldehyde, forming in the free form or in the form of the dimethylacetal, from the homologization of methanol, in a very economical and industrially very simple manner from the homologization mixture by distillation, and at the same time to recover the methanol.

We have found that this object is achieved and that acetaldehyde and methanol can be isolated in an economical and industrially simple manner, by distillation, from reaction mixtures which result from the homologization of methanol and which in addition to acetaldehyde essentially contain acetaldehyde dimethylacetal, methanol, methyl acetate and water, by a process wherein (a) the reaction mixture is introduced into the middle zone of a column I, at a temperature at which the methyl acetate and its azeotropic mixture with methanol vaporize completely, but the methanol does not, ($b_1$) a liquid aqueous acid, fed into the upper quarter of the column I, is led in counter-current to the rising vapors and causes cleavage of the acetaldehyde dimethylacetal into acetaldehyde and methanol, or ($b_2$) instead of the aqueous acid, water alone is used, and the acetal cleavage is effected by means of a solid acidic ion exchanger, (c) a vapor mixture of methyl acetate and acetaldehyde is taken off at the top of column I and separated into its components in a column II, (d) in the lower quarter of column I, a liquid mixture of methanol and water is taken off and is separated into its components in a column III, and (e) a part of the aqueous acid (embodiment $b_1$) or of the water (embodiment $b_2$) arising in the bottom of column I is removed, together with minor amounts of other products, from the system, and the remainder of this aqueous acid or of this water is combined with the water forming in the bottom of column III and the combined aqueous solution, after mixing with an acid, is recycled into the upper quarter of column I.

The process according to the invention, employing embodiment ($b_1$), is illustrated in FIG. 1, which is directly intelligible from the process definition given above and therefore requires no further explanation.

Figure 2:
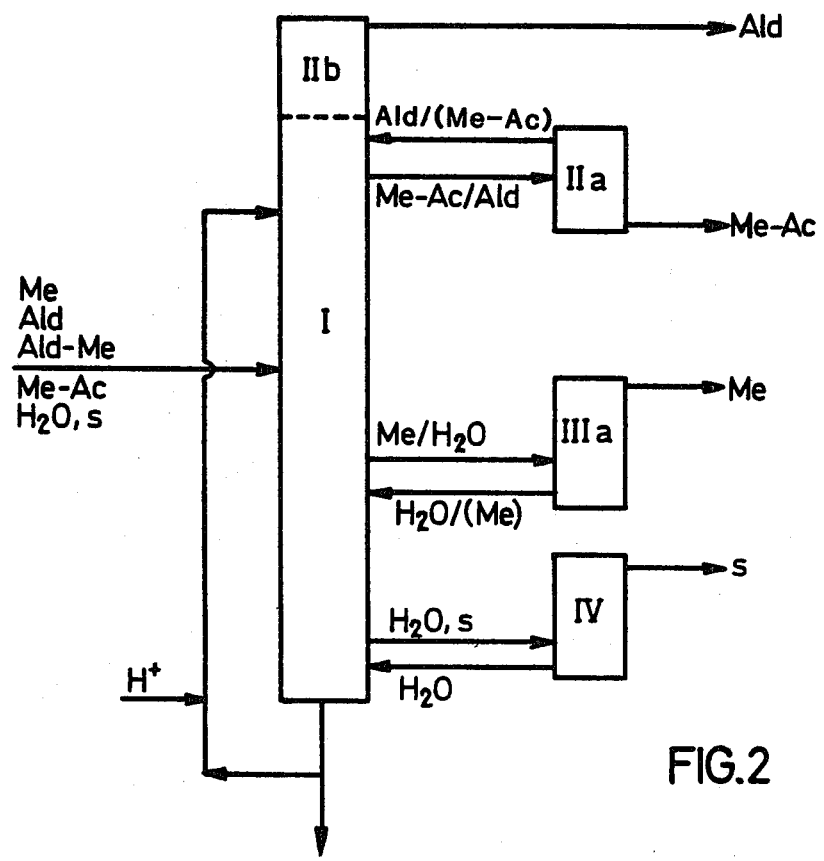

FIG. 2 shows different versions of this embodiment, in which, compared to the basic arrangement shown in FIG. 1, Column II is shortened to constitute purely a stripping column IIa and conversely column I is lengthened at the top, by addition of section IIb, so that the acetaldehyde/methyl acetate fractionation is shifted into main column I, and/or Column III is shortened to constitute purely a rectifying column IIIa and as a result the water/methanol fractionation is also shifted into main column I, and/or the other products, such as ethanol, $C_3$- and $C_4$-alcohols and $C_3$- and $C_4$-aldehydes, are separated from water by distillation in a column IV.

If the novel process is carried out under atmospheric pressure, the boiling points of the compounds and azeotropes involved ensure that the temperature is 100°–120° C. in the bottom of column I, 60°–75° C. in the middle of the same column, and 21°–35° C. at the top of this column. The temperature profiles of the other columns II and III or IIa, IIIa and IV follow in a corresponding manner.

Since, however, acetaldehyde boils at 21° C. and therefore cannot be condensed with normal cooling water, it is preferred to run the process under a pressure of 2–4 bar, at which acetaldehyde boils at 40°–65° C. and can therefore be condensed by means of normal cooling water.

The number of theoretical plates is advantageously 25–60 in column I, 5–15 in column II, 10–30 in column III and 10–30 in column IV. If the alternative methods of isolating methyl acetate and methanol illustrated in FIG. 2 are employed, column IIa and IIIa have respectively 5–10 and 8–30 theoretical plates, and the number of theoretical plates of column I is correspondingly increased by 3–10 at the top (IIb).

The exact construction of the columns is immaterial, so that it is preferred to use packed columns, which are cheap.

The process according to the invention is in principle independent of the homologization reaction, ie. it would succeed even with high proportions of ethanol. In that case, it would simply be essential to carry out the distillation in column IV. Since, however, in accordance with the object of the invention, the main concern is the economical isolation of acetaldehyde, the homologization would tend to be carried out under conditions such that only little ethanol forms. This can be achieved if the synthesis gas contains not more than 55% by volume of hydrogen and if the methanol conversion is at about 40%. In other respects, the homologization can be carried out in a conventional manner, ie. under a pressure of from 100 to 700 bar, at 150°–210° C., and in the presence of from 0.1 to 2.0% by weight, based on the total amount of reaction mixture in the reactor, of a homologization catalyst.

Such catalysts are carbonyl complexes of metals of group VIII of the periodic table, and of rhenium. In general, particularly suitable compounds are those also employed for hydroformylation, ie. especially rhodium complexes and cobalt complexes. It is possible to employ the carbonyl complexes, such as $Co_2(CO)_8$, or, preferably, to employ compounds of the particular metals, such as rhodium oxide, rhodium acetate or cobalt acetate, since the complexes form in situ under the reaction conditions. The stability of the complexes can be increased by employing additional ligands such as acetylacetone, tertiary phosphines or phosphites. Where the metal complexes are relatively non-volatile, they remain in the reactor when the reaction mixture is taken off as a gas. If on the other hand the complexes are volatile, the catalysts must be destroyed in a conventional manner, in a separate process step, for example by treatment with an aqueous acid, after which the reaction mixture is distilled off, leaving the inorganic constituents. Another possibility is to destroy the complexes oxidatively by treatment with air.

An essential feature of the process according to the invention is the step $(b_1)$ or $(b_2)$, ie. the cleavage of the acetaldehyde dimethylacetal by means of an acid in the upper half of column I. Since there only little excess methanol is present, and the volatile acetaldehyde immediately escapes upwards, the acetal cannot re-form, which it would if the acetal cleavage were carried out in, for example, the bottom of the column.

The acid used can be any strong acid, for example sulfuric acid, hydrochloric acid, nitric acid, formic acid or a sulfonic acid, eg. p-toluenesulfonic acid, the concentrations being about 0.01–10% by weight.

Since water is formed continuously during the synthesis, a proportion of the water must constantly be removed (discharged) from the water circuit in column I, in the course of which a corresponding proportion of the acid and possibly also of the other products—if distillation IV is not carried out—is lost. Accordingly, the acid must be continuously replaced by the proportion lost with the discharged water, as is shown in the Figures.

In embodiment $(b_2)$, there is no consumption of acid if the acid used is an ion exchanger, which can be located in the middle zone of column I. However, it is technologically more advantageous to bring the mixture from column I into contact with an ion exchanger outside the column by taking off a proportion of the mixture at one or more points, passing it over the ion exchanger outside the column, and returning it into the column, in each case at the level at which it was taken off. The water circuit is unaffected by the use of the ion exchanger, because the water is required for the acetal cleavage.

Process step (c) deserves particular comment. It would have been expected that at the top of column I the azeotrope of methyl acetate and methanol (boiling point 53° C. under atmospheric pressure) would arise, so that these two compounds could no longer be separated from one another without considerable expense. However, the acetaldehyde breaks this azeotrope, so that the top product obtained is a mixture of acetaldehyde and methyl acetate, the separation of which, in column II, presents no problems. Small amounts of methanol, which under certain circumstances can also be formed at the top of the column, can be removed by employing the embodiment shown in FIG. 2, since the top product of column IIa, which consists of acetaldehyde, a small amount of methyl acetate and, in the present case, a small amount of methanol, is returned to column I.

Since the process according to the invention breaks the methanol/methyl acetate azeotrope, the recovery of methanol from its mixture with water no longer presents any difficulties. Accordingly, further comments on process step (d), which relates to separating the methanol/water mixture, are unnecessary. The same is true of process step (e) and of the embodiment in which the other products—if they are not to be discarded with the water discharged from the system—are recovered as distillate from the additional column IV.

EXAMPLE

This Example was carried out in a trial apparatus as shown in FIG. 1, under atmospheric pressure. All the columns were constructed as packed columns. Column I was 2 m high and had an internal diameter of 5 cm and 40 theoretical plates. Column II was 1 m high and had an internal diameter of 5 cm and 20 theoretical plates, and column III was 0.8 high and had an internal diameter of 5 and 12 theoretical plates. At the height of the 30th theoretical plate (counted from the bottom), at which the temperature was 61° C., 300 g per hour of reaction mixture resulting from the homologization of methanol were fed to column I.

The homologization was carried out at 300 bar and 125° C. in the presence of 0.3% by weight, based on the reactor contents, of cobalt in the form of cobalt acetate, and using a mixture of 50% by volume of hydrogen and 50% by volume of carbon monoxide, the methanol conversion being kept at about 26%. After releasing the pressure, the reaction mixture obtained was treated with air, which destroyed the cobalt complex. The mixture was then distilled off, leaving the cobalt salt formed. The mixture had the following composition:
 54% by weight (162 g) of methanol
 7% by weight (21 g) of acetaldehyde
 9% by weight (27 g) of acetaldehyde dimethylacetal
 7% by weight (21 g) of methyl acetate
 15% by weight (45 g) of water
 6% by weight (18 g) of ethanol
 2% by weight (6 g) of other products.
100 per hour of 1% strength by weight aqueous sulfuric acid, additionally containing a small amount of ethanol and other products, were introduced into column I at the level of the 35th plate (48° C.).

Using a reflux ratio of 5, the material taken off per hour at the top of the column (29° C.) contained 34 g of acetaldehyde, 21 g of methyl acetate, 0.5 g of acetaldehyde dimethylacetal and 0.1 g of methanol. This mixture was separated, in column II, into acetaldehyde (yield virtually 100%) and only slightly contaminated methyl acetate. A side stream of vapor was taken off column I at the level of the 15th plate (75° C.) and was separated, in column III, into 181 g of methanol as top product and 64 g of a bottom product which consisted of 40 g of water, 18 g of ethanol and 6 g of other products.

This bottom product was combined with the bottom product of column I (110° C.), which consisted of 100 g of aqueous sulfuric acid, after which 64 g of the combined bottom products were discharged from the system. Thereafter, a small amount of sulfuric acid was again added to the system in order to keep the acid concentration constant.

We claim:

1. A process for isolating acetaldehyde and methanol from a reaction mixture which results from the homologization of methanol and which in addition to acetaldehyde essentially contains acetaldehyde dimethylacetal, methanol, methyl acetate and water, which process comprises:
    (a) introducing the reaction mixture into the middle zone of a column I, at a temperature at which the methyl acetate and its azeotropic mixture with methanol vaporize completely, but the methanol does not,
    ($b_1$) feeding a liquid aqueous acid into the upper quarter of the column I in counter-current to the rising vapors to cause cleavage of the acetaldehyde-dimethylacetal into acetaldehyde and methanol, or
    ($b_2$) in place of step ($b_1$), feeding water alone into the upper quarter of the column I in counter-current to the rising vapors in the presence of a solid acidic ion exchanger to effect the acetal cleavage,
    (c) taking off a vapor mixture of methyl acetate and acetaldehyde at the top of column I and separating the mixture into its components in a column II,
    (d) in the lower quarter of column I, taking off a liquid mixture of methanol and water and separating the mixture into its components in a column III, and
    (e) removing a part of the aqueous acid (embodiment $b_1$) or of the water (embodiment $b_2$) arising in the bottom of column I, together with minor amounts of other products, from the system, and combining the remainder of this aqueous acid or of this water with the water forming in the bottom of column III and recycling the combined aqueous solution, after mixing with an acid, into the upper quarter of column I.

2. The process of claim 1, wherein, in place of column II, a stripping column IIa is used, in which the acetaldehyde/methyl acetate mixture is fed into the upper zone, the mixture depleted in methyl acetate and containing principally acetaldehyde is taken from the top of column IIa and returned to column I, the greater part of the methyl acetate is taken from the bottom of column IIa and the separation of the methyl acetate/acetaldehyde mixture returned to column I is effected in an additional column section IIb attached to the top of column I.

3. The process of claim 2, wherein column III is replaced by a rectifying column IIIa, in which the methanol/water mixture is introduced into the lower zone, the mixture depleted in methanol and principally containing water is returned from the bottom of column IIIa to column I, and the greater part of the methanol is taken off the top of column IIIa.

4. The process of claim 2, wherein the other products, which accumulate, as a mixture with the aqueous acid or with water, in the lower zone of column I, are separated from water by distilling a side stream in a column IV.

5. The process of claim 1, wherein column III is replaced by a rectifying column IIIa, in which the methanol/water mixture is introduced into the lower zone, the mixture depleted in methanol and principally containing water is returned from the bottom of column IIIa to column I, and the greater part of the methanol is taken off the top of column IIIa.

6. The process of claim 5, wherein the other products, which accumulate, as a mixture with the aqueous acid or with water, in the lower zone of column I, are separated from water by distilling a side stream in a column IV.

7. The process of claim 1, wherein the other products, which accumulate, as a mixture with the aqueous acid or with water, in the lower zone of column I, are separated from water by distilling a side stream in a column IV.

* * * * *